(12) United States Patent
Chen et al.

(10) Patent No.: US 9,174,951 B2
(45) Date of Patent: Nov. 3, 2015

(54) GLUCOSE TRANSPORTER INHIBITORS

(71) Applicant: The Ohio State University Research Foundation, Columbus, OH (US)

(72) Inventors: Ching-Shih Chen, Upper Arlington, OH (US); Dasheng Wang, Dublin, OH (US); Samuel K. Kulp, Hillard, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 0 days.

(21) Appl. No.: 14/386,127

(22) PCT Filed: Mar. 28, 2013

(86) PCT No.: PCT/US2013/034338
§ 371 (c)(1),
(2) Date: Sep. 18, 2014

(87) PCT Pub. No.: WO2013/148994
PCT Pub. Date: Oct. 3, 2013

(65) Prior Publication Data
US 2015/0051255 A1    Feb. 19, 2015

Related U.S. Application Data

(60) Provisional application No. 61/616,496, filed on Mar. 28, 2012.

(51) Int. Cl.
*C07D 277/34*    (2006.01)
(52) U.S. Cl.
CPC .................................... *C07D 277/34* (2013.01)
(58) Field of Classification Search
USPC ........................................................ 548/183
See application file for complete search history.

(56) References Cited

U.S. PATENT DOCUMENTS

2009/0291992 A1* 11/2009 Chen et al. ..................... 514/369
2011/0086895 A1*  4/2011 Chen et al. ..................... 514/369
2011/0088689 A1   4/2011 Helie et al.

OTHER PUBLICATIONS

Wang et al., Journal of Medicinal Chemistry, Apr. 2, 2012, 55(8), pp. 3827-3836.*
Macheda et al., Journal of Cellular Physiology, 2005, vol. 202, pp. 654-662.*
Golub et al., Science, vol. 286, Oct. 15, 1999, pp. 531-537.*
Younes et al. "Wide Expression of the Human Erythrocyte Glucose Transporter Glut1 in Human Cancers" Cancer Res, vol. 56, pp. 1164-1167, 1996.
Wei et al. "Energy Restriction as an Antitumor Target of Thiazolidinediones" J. Biol. Chem., 285:9780-9791, 2010.
Pelicano et al., "Glycolysis Inhibition for Anticancer Treatment", Oncogene, vol. 25, 2006, pp. 4633-4646.
Salas-Burgos et al., "Predicting the Three-Dimensional Structure of the Human Fracititative Glucose Transporter Glut1 by a Novel Evolutionary Homology Strategy: Insights on the Molecular Mechanism of Substrate Migration, and Binding Sites for Gluose and Inhibitory Molecules" Biophysical Journal, vol. 87, 2004, pp. 2990-2999.
Wood et al., "A Novel Inhibitor of Glucose Uptake Sensitizes Cells to FAS-Induced Cell Death" Mol. Cancer Ther., vol. 7, 2008, pp. 3546-3555.
Shanmugam et al., "Targeting Glucose Consumption and Autophagy in Myeloma with the Novel Nucleoide Analogue 8-Aminoadenosine" Journal of Biological Chemistry, vol. 284. No. 39, 2009, pp. 26816-26830.
Wei et al., "Thiazolidinediones Mimic Glucose Starvation in Facilitating Sp1 Degradation Through the Up-Regulation of β-Transducin Repeat-Containing Protein" Molecular Pharmacology, vol. 76, No. 1, 2009, pp. 47-57.
Chen et al., "Energy Restriction-Mimetic Agents Induce Apoptosis in Prostate Cancer Cells in Part through Epigenetic Activation of KLF6 Tumor Suppressor Gene Expression" Journal of Biological Chemistry, vol. 286, No. 12, 2011, pp. 9968-9976.
Park, "Inhibition of Glucose and Dehydraoscorbio Acid Uptakes by Resveratrol in Human Transformed Myelocytic Cells" J. Nat. Prod., vol. 64, 2001, pp. 381-384.
Harmon et al., "Naringenin Inhibits Glucose Uptake in MCF-7 Breast Cancer Cells: A Mechanism for Impaired Cellular Proliferation" Breast Cancer Research and Treatment, vol. 85, 2004, pp. 103-110.
Cao et al., Glucose Uptake Inhibitor Sensitizes Cancer Cells to Daunorubicin and Overcome Drug Resistance in Hypoxia Cancer Chemother Pharmacol, vol. 59, 2007, pp. 495-505.
Yang et al., "Pharmacological Exploitation of the Peroxisome Proliferator-Activated Receptor γ Agonist Ciglitazone to Develop a Novel Class of Androgen Receptor-Ablative Agents" J. Med. Chem., vol. 51, 2008, pp. 2100-2107.

* cited by examiner

*Primary Examiner* — Laura L. Stockton
(74) *Attorney, Agent, or Firm* — Tarolli, Sundheim, Covell & Tummino LLP

(57) ABSTRACT

Thiazolidinedione compounds and pharmaceutically acceptable salts thereof are described. The compounds can be used in methods of treating cancer in a subject by administering to the subject a therapeutically effective amount of the compound. The compounds can also be used in methods of inhibiting glucose uptake in a cell by contacting the cell with the compound.

15 Claims, 8 Drawing Sheets

GLUCOSE TRANSPORTER INHIBITORS

CONTINUING APPLICATION DATA

This application is the U.S. national phase entry of PCT/US2013/034338, with an international filing date of Mar. 28, 2013, which claims priority from U.S. Provisional Application Ser. No. 61/616,496, filed Mar. 28, 2012, the entire contents of which are incorporated herein by reference.

GOVERNMENT FUNDING

The present invention was supported, at least in part, by government support by the Nation Institutes of Health under Grant No. RO1CA112250 and the Department of Defense Prostate Cancer Research Program Grant No. W8XWH-09-0198. The U.S. Government therefore has certain rights in this invention.

BACKGROUND

Cancer cells gain growth advantages in the microenvironment by shifting cellular metabolism from oxidative phosphorylation to glycolysis, the so-called Warburg effect. This glycolytic shift enables cancer cells to adapt to low-oxygen microenvironments, to generate biosynthetic building blocks for cell proliferation, to acidify the local environment to facilitate tumor invasion, and to generate NADPH and glutathione through pentose phosphate shunt to increase resistance to oxidative stress. Kroemer, G.; Pouyssegur, J., Cancer Cell, 13, 472-82 (2008). Thus, the Warburg effect is considered as a fundamental property of neoplasia, thereby constituting the basis for tumor imaging by [$^{18}$F]2-fluoro-2-deoxyglucose positron emission tomography.

From a therapeutic perspective, targeting glycolysis by blocking glucose uptake represents a clinically relevant strategy for cancer treatment, which has constituted the focus of many investigations. To date, a number of small-molecule agents with the capability to suppress the activity/expression of glucose transporters have been reported, including resveratrol (Park, J. B. J Nat Prod, 64, 381-4 (2001)), naringenin (Harmon et al., Breast Cancer Res Treat, 85, 103-10 (2004)), phloretin (Cao et al., Cancer Chemother Pharmacol, 59, 495-505 (2007)), fasentin (Wood et al., Mol Cancer Ther, 7, 3546-55 (2008)), 8-aminoadenosine (Shamnugam et al., J Biol Chem, 284, 26816-30 (2009)), and STF-31.13. Exposure of cancer cells to these agents gave rise to reduced cell proliferation and/or chemosensitization, providing a proof-of-concept that targeting glucose transporters represents a therapeutically relevant strategy for cancer treatment.

It has previously been demonstrated that the suppressive effects of the peroxisome proliferator-activated receptor (PPAR)γ agonist ciglitazone (1), shown in FIG. 1, on various signaling pathways, including those mediated by cyclin D1, Sp1, and androgen receptor (AR), in prostate cancer cells was attributable to its ability to block glucose entry independently of PPARγ. Wei et al., J Biol Chem, 285, 9780-91 (2010); Wei et al., Mol Pharmacol, 76, 47-57 (2009).

The pharmacological exploitation of the PPARγ-inactive analogue of compound 1, (Z)-5-(4-[(1-methylcyclohexyl)methoxy]benzylidene)-thiazolidine-2,4-dione (Δ2CG, 2), as a scaffold to develop androgen receptor (AR)-ablative agents via its permuted isomer 3 has been reported, which led to (Z)-5-(4-hydroxy-3-(trifluoromethyl)benzylidene)-3-((1-methylcyclohexyl) methyl)thiazolidine-2,4-dione (CG-12, 4) as the optimal compound (FIG. 1A). Yang et al., J Med Chem, 51, 2100-7 (2008). However, there remains a need for new energy restriction mimetic agents, particularly those exhibiting increased potencies.

SUMMARY OF THE INVENTION

Based on the inventors finding that the antitumor effect of ciglitazone, a thiazolidinedione peroxisome proliferator-activated receptor (PPAR)γ agonist, was in part attributable to its ability to block glucose uptake independently of PPARγ, the PPARγ-inactive analogue was used to develop a novel class of glucose transporter inhibitors. This lead optimization led to compound 30 (5-(4-hydroxy-3-trifluoromethylbenzylidene)-3-[4,4,4-trifluoro-2-methyl-2-(2,2,2-trifluoroethyl)-butyl]-thiazolidine-2,4-dione) as the optimal agent. Compound 30 exhibited high potency in inducing apoptotic death in LNCaP prostate cancer cells through the suppression of glucose uptake ($IC_{50}$, 2.5 µM). Equally important, thiazolidinedione compounds (e.g., compound 30) displayed no appreciable cytotoxicity in prostate and mammary epithelial cells. Evidence suggests that this glucose uptake inhibition was associated with the inhibition of glucose transporter (GLUT)1 ($IC_{50}$, 2 µM), the predominant GLUT isoform expressed in LNCaP cells. Moreover, the mechanism of antitumor action of the thiazolidinedione derivatives was validated by its effect on a series of energy restriction-associated cellular responses, reminiscent with that of its parent compounds. Moreover, homology modeling analysis suggests that the inhibitory effect of the compounds on glucose entry was attributable to its ability to bind to the Glut1 channel at a unique site distinct from that of glucose.

Accordingly, in one aspect, the invention provides a set of compounds according to formula I:

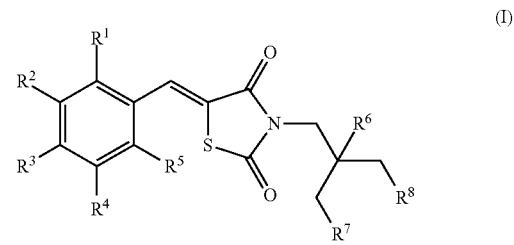

wherein $R^1$-$R^5$ are selected from the group consisting of hydrogen, $C_1$-$C_4$ alkyl, halogen, hydroxyl, nitro, amine, $C_1$-$C_4$ alkoxy, and trifluoromethyl; $R^6$ is selected from the group consisting of hydrogen, halogen, and $C_1$-$C_4$ alkyl; and $R^7$ and $R^8$ are $C_1$-$C_4$ alkyl, $C_1$-$C_4$ cycloalkyl, or trifluoromethyl; and pharmaceutically acceptable salts thereof.

In another aspect, the invention provides a method of treating cancer in a subject in need thereof. The method includes administering to the subject a therapeutically effective amount of a compound according to Formula I:

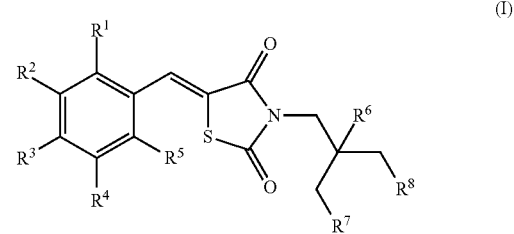

wherein $R^1$-$R^5$ are selected from the group consisting of hydrogen, $C_1$-$C_4$ alkyl, halogen, hydroxyl, nitro, amine, $C_1$-$C_4$ alkoxy, and trifluoromethyl; $R^6$ is selected from the group consisting of hydrogen, halogen, and $C_1$-$C_4$ alkyl; and $R^7$ and $R^8$ are $C_1$-$C_4$ alkyl, $C_1$-$C_4$ cycloalkyl, or trifluoromethyl; and pharmaceutically acceptable salts thereof.

In some embodiments of the methods of treating cancer, the subject is a human. In further embodiments, the compound is administered in a pharmaceutically acceptable carrier. In yet further embodiments the cancer is a glucose receptor overexpressing cancer (e.g., GLUT1 overexpression), while in yet additional embodiments the cancer is selected from the group consisting of prostate cancer, breast cancer, and pancreatic cancer.

Another aspect of the invention provides a method of inhibiting glucose uptake in a cell by contacting the cell with a compound of formula I:

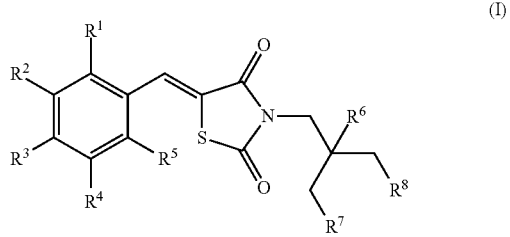

(I)

wherein $R^1$-$R^5$ are selected from the group consisting of hydrogen, $C_1$-$C_4$ alkyl, halogen, hydroxyl, nitro, amine, $C_1$-$C_4$ alkoxy, and trifluoromethyl; $R^6$ is selected from the group consisting of hydrogen, halogen, and $C_1$-$C_4$ alkyl; and $R^7$ and $R^8$ are $C_1$-$C_4$ alkyl, $C_1$-$C_4$ cycloalkyl, or trifluoromethyl; and pharmaceutically acceptable salts thereof. In some embodiments, the compound inhibits GLUT1-mediated glucose uptake. Embodiments of inhibiting glucose uptake in a cell include embodiments in which the cells are either in vivo or in vitro.

BRIEF DESCRIPTION OF THE FIGURES

The present invention may be more readily understood by reference to the following drawings, wherein.

DETAILED DESCRIPTION OF THE INVENTION

Figure 1:
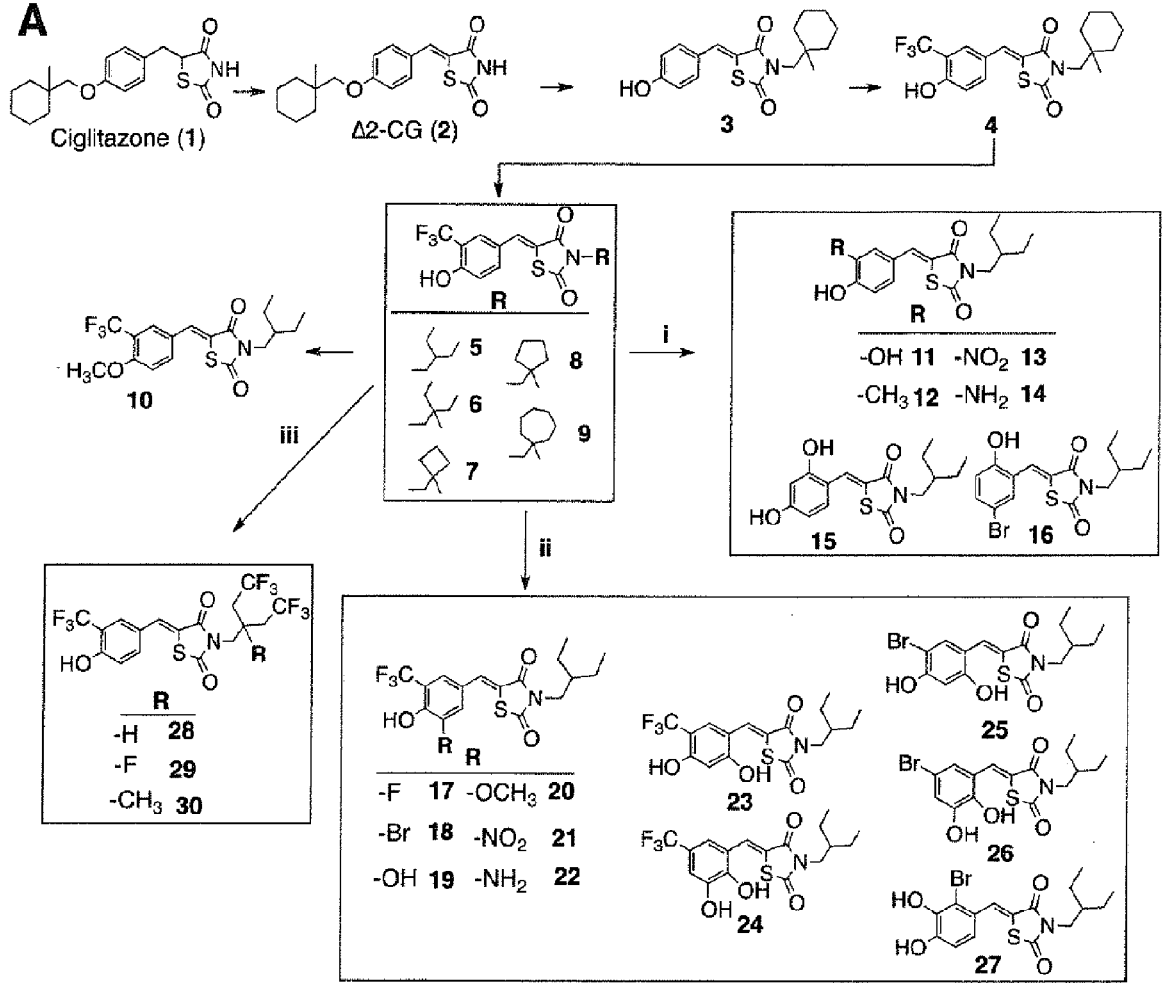
FIG. 1. (A) Chemical structures of compounds 1-30 in the ciglitazone-based focused compound library. (B) General synthetic procedure for compounds 5-30. Reaction conditions: a, DIPAD, TPP/dry THF; b, piperidine, ethanol/reflux.
Figure 1:
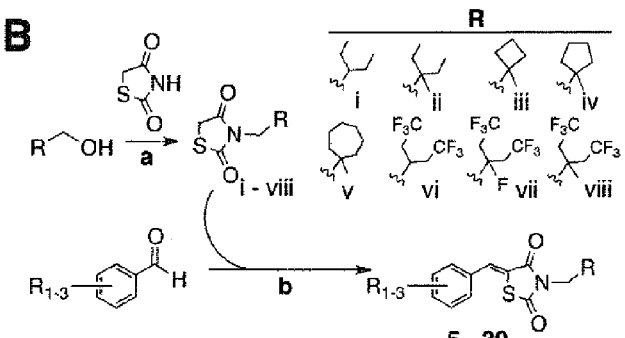

The present invention provides a number of thiazolidinedione derivatives. These thiazolidinedione derivatives have been shown to be effective for inhibiting glucose uptake in a cell by inhibiting glucose transporters. The thiazolidinedione derivatives have also been shown to provide a method of treating cancer in a subject. Studies have been carried out to identify compounds having particularly high activity, some of which show activity many fold higher than previously identified compounds while exhibiting no appreciable cytotoxicity against normal cells.

The proof of concept of the optimization of thiazolidinedione derivatives for glucose uptake inhibition was provided by compound 30, which exhibited high potency in inducing apoptotic death in LNCaP cells through the suppression of glucose uptake ($IC_{50}$, 2.5 µM). Evidence suggests that this suppression of glucose entry was associated with the inhibition of glucose transporter (GLUT)1 ($IC_{50}$, 2 µM), the predominant GLUT isoform expressed in LNCaP cells. Moreover, the mechanism of antitumor action of compound 30 was validated by its effect on a series of energy restriction-associated cellular responses, reminiscent with that of its parent compounds.

DEFINITIONS

The terminology as set forth herein is for description of the embodiments only and should not be construed as limiting of the invention as a whole. As used in the description of the invention and the appended claims, the singular forms "a", "an", and "the" are inclusive of their plural forms, unless contraindicated by the context surrounding such.

As used herein, the term "organic group" is used to mean a hydrocarbon group that is classified as an aliphatic group, cyclic group, or combination of aliphatic and cyclic groups (e.g., alkaryl and aralkyl groups). In the context of the present invention, suitable organic groups for thiazolidinediones of this invention are those that do not interfere with the energy restriction activity of the thiazolidinediones. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups. Unless otherwise specified, these groups contain from 1 to 20 carbon atoms, with alkenyl groups, containing from 2 to 20 carbon atoms. In some embodiments, these groups have a total of at most 10 carbon atoms, at most 8 carbon atoms, at most 6 carbon atoms, or at most 4 carbon atoms. Alkyl groups including 4 or fewer carbon atoms can also be referred to as lower alkyl groups. The number of carbons can be indicated using $C_X$, wherein X is the number of carbons included in the alkyl group.

Cycloalkyl, as used herein, refers to an alkyl group (i.e., an alkyl, alkenyl, or alkynyl group) that forms a ring structure. Cyclic groups can be monocyclic or polycyclic and preferably have from 3 to 10 ring carbon atoms. A cycloalkyl group can be attached to the main structure via an alkyl group including 4 or less carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. Halo moieties include chlorine, bromine, fluorine, and iodine.

The term "aryl" as used herein includes carbocyclic aromatic rings or ring systems. Examples of aryl groups include phenyl, naphthyl, biphenyl, fluorenyl and indenyl. Aryl groups may be substituted or unsubstituted.

Unless otherwise indicated, the term "heteroatom" refers to the atoms O, S, or N. The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

When a group is present more than once in any formula or scheme described herein, each group (or substituent) is independently selected, whether explicitly stated or not. For example, for the formula —C(O)—NR$_2$ each R group is independently selected.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

The invention is inclusive of the compounds described herein in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

The term thiazolidinedione derivatives, as used herein, is a shorthand for the thiazolidinedione compounds of the invention, as described by the formulas provided herein; and is not meant to encompass all possible compounds that might be characterized as a thiazolidinedione by one skilled in the art.

"Treat", "treating", and "treatment", etc., as used herein, refer to any action providing a benefit to a subject at risk for or afflicted with a condition or disease such as cancer, including improvement in the condition through lessening or suppression of at least one symptom, delay in progression of the disease, etc. The subject may be at risk due to exposure to carcinogenic agents, being genetically predisposed to disorders characterized by unwanted, rapid cell proliferation, and so on.

"Pharmaceutically acceptable" as used herein means that the compound or composition is suitable for administration to a subject for the methods described herein, without unduly deleterious side effects in light of the severity of the disease and necessity of the treatment.

The terms "therapeutically effective" and "pharmacologically effective" are intended to qualify the amount of each agent which will achieve the goal of improvement in disease severity and the frequency of incidence over treatment of each agent by itself, while avoiding adverse side effects typically associated with alternative therapies.

Thiazolidinedione Derivatives

A variety of thiazolidinedione derivatives are described herein. In one aspect, the invention provides a number of compounds according to formula I:

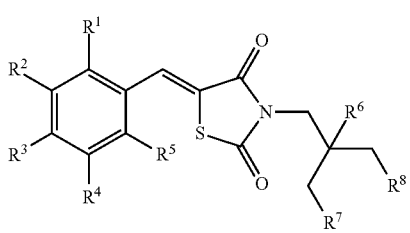

wherein $R^1$-$R^5$ are selected from the group consisting of hydrogen, $C_1$-$C_4$ alkyl, halogen, hydroxyl, nitro, amine, $C_1$-$C_4$ alkoxy, and trifluoromethyl; $R^6$ is selected from the group consisting of hydrogen, halogen, and $C_1$-$C_4$ alkyl; and $R^7$ and $R^8$ are $C_1$-$C_4$ alkyl, $C_1$-$C_4$ cycloalkyl, or trifluoromethyl; and pharmaceutically acceptable salts thereof.

All other possible subsets of compounds described by formula I are also included in embodiments of the invention provided herein. For example, in some embodiments, $R^1$ and $R^5$ are hydrogen, while in further embodiments $R^1$, $R^4$, and $R^5$ are hydrogen.

Compounds 28-30 exhibit high potency as GLUT1 inhibitors, as further described herein. These compounds are examples of compounds of formula I wherein $R^7$ and $R^8$ are trifluoromethyl. Accordingly, compounds wherein $R^7$ and $R^8$ are trifluoromethyl moieties are a preferred embodiment of the invention. Alternately, $R^7$ and $R^8$ are $C_1$-$C_4$ alkyl or $C_1$-$C_4$ cycloalkyl. An example of a suitable cycloalkyl group is a fluoro cyclopropyl group. Further embodiments of compounds including trifluoromethyl groups at $R^7$ and $R^8$ are further defined by $R^1$, $R^4$, and $R^5$ being hydrogen. In yet further embodiments, of these compounds, $R^2$ is trifluoromethyl and $R^3$ is hydroxyl.

A preferred compound of formula I is compound 30 (5-(4-Hydroxy-3-trifluoromethyl-benzylidene)-3-[4,4,4-trifluoro-2-methyl-2-(2,2,2-trifluoro-ethyl)-butyl]-thiazolidine-2,4-dione), which has the structure shown:

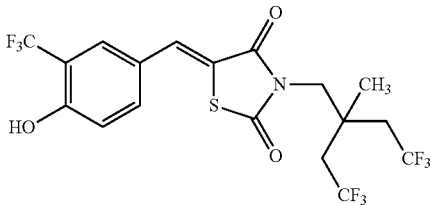 [SMILES: CC(CN1C(=O)S/C(=C\c2ccc(O)c(C(F)(F)F)c2)C1=O)(CC(F)(F)F)CC(F)(F)F]

Energy Restriction Mimetic Agents

In another aspect of the invention, the thiazolidinedione derivatives can be used as energy restriction mimetic agents. The restriction of energy metabolism refers to an effect that can be produced, for example, by dietary energy restriction, such as limited calorie intake (i.e., caloric restriction). Dietary energy restriction results in reduced glucose availability, resulting in a decrease in glucose metabolism and glycolysis. Glycolysis is a series of metabolic processes by which one molecule of glucose is catabolized to two molecules of pyruvate to provide a net gain of two ATP molecules. In normal cells, glycolysis provides the initial step of cellular energy production and is a precursor to the tricarboxylic acid cycle, which is carried out in the mitochondria and generates a substantially larger amount of ATP per glucose molecule.

Restriction of energy metabolism can also be mimicked by administering suitable compounds, referred to as energy restriction mimetic agents. For example, 2-deoxyglucose can restrict energy metabolism as a result of being phosphorylated by hexokinase, which is then trapped in the phosphorylated state which accumulates and prevents further glucose metabolism. The experiments carried out by the inventors and described herein demonstrate that thiazolidinedione derivatives are capable of functioning as energy restriction mimetic agents by suppressing glucose uptake through the inhibition of glucose transporters. A preferred glucose transporter for inhibition by the compounds of the present invention is GLUT1. The antiproliferative potency of these compounds has also been shown to be associated with their ability to elicit energy restriction associated cellular responses. Additional details are provided by Example 1, herein.

Accordingly, a further aspect of the invention provides a method of inhibiting glucose uptake in a cell by contacting the cell with a compound of formula I:

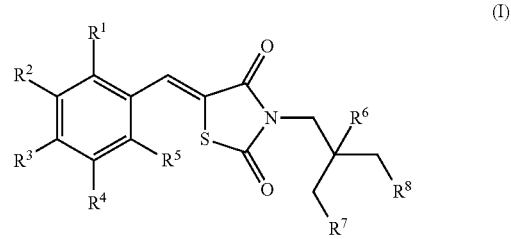

wherein $R^1$-$R^5$ are selected from the group consisting of hydrogen, $C_1$-$C_4$ alkyl, halogen, hydroxyl, nitro, amine, $C_1$-$C_4$ alkoxy, and trifluoromethyl; $R^6$ is selected from the group consisting of hydrogen, halogen, and $C_1$-$C_4$ alkyl; and $R^7$ and $R^8$ are $C_1$-$C_4$ alkyl, $C_1$-$C_4$ cycloalkyl, or trifluoromethyl; and pharmaceutically acceptable salts thereof.

Contacting the cell refers to placing the compound in an environment where the compound can be expected to come into contact with the cells within a reasonable period of time. While not intending to be bound by theory, it is believed that the compounds inhibit glucose uptake by binding to glucose transporter molecules present on the surface of the cell, thereby inhibiting the activity of those transporters. For example, in some embodiments, the compound inhibits GLUT1-mediated glucose uptake by binding to the GLUT1 glucose transporter.

The cells referred to herein are animal cells of interest which either express or overexpress glucose transporters. The cells can be healthy cells, or the cells can be diseased cells such as cancer cells. In different embodiments, the cell can be either in vivo or the cell can be in vitro. In vitro cells are cells of an organism that have been isolated from their usual biological context and placed in an artificial environment. An example of in vitro cells are tissue culture cells. In vivo cells, on the other hand, are cells that are part of a living organism. For example, cancer cells in an animal subject are in vivo cells.

All of the compounds encompassed by formula I are considered to be described herein, and are suitable for inhibiting glucose uptake by a cell. In some embodiments, the compounds of formula I are further defined such that $R^1$, $R^4$, and $R^5$ are hydrogen. In other embodiments $R^7$ and $R^8$ are trifluoromethyl, while in other embodiments $R^7$ and $R^8$ are $C_1$-$C_4$ alkyl or $C_1$-$C_4$ cycloalkyl. In yet further embodiments, $R^2$ is trifluoromethyl and $R^3$ is hydroxyl.

In a preferred embodiment, compound 30, which is the structure shown below, is used for inhibiting glucose uptake by a cell:

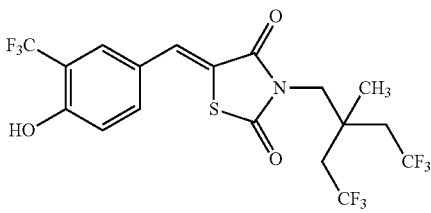 [SMILES: CC(CN1C(=O)S/C(=C\c2ccc(O)c(C(F)(F)F)c2)C1=O)(CC(F)(F)F)CC(F)(F)F]

Inhibition of glycolysis results in the restriction of energy metabolism. Glycolysis is the metabolic pathway that converts glucose into pyruvate, resulting in the release of the high energy compounds, ATP and NADH. Any amount of decrease in the normal level of glycolysis represents a restriction of energy metabolism with respect to the invention described herein. However, different embodiments of the invention may result in varying levels of inhibition. For example, administering a thiazolidinedione derivative can result in a 10%, 20%, 30%, 40%, 50%, 60%, 70%, 80%, 90%, or complete inhibition of glycolysis, or any other significant level of inhibition within this range of numbers. The level of inhibition achieved can vary with the dose of thiazolidinedione derivative used, and is therefore dose dependent. While high levels of glycolysis inhibition can be achieved, it should be noted that more moderate levels, i.e., 50% inhibition or less, is generally more clinically useful as this avoids the potential toxicity of high levels of glycolysis inhibition.

While the inhibition of glycolysis can be measured using a variety of different compounds and effects known to those skilled in the art, examples of markers that are commonly used to measure decreases in glycolysis are the decreased rate of glucose uptake by cells, decreases in the formation of NADH and lactate, and an increase in autophagy, which can be identified by a corresponding increase in autophagosome formation.

The inhibition of glycolysis in a subject can have one or more beneficial effects. For example, inhibition of glycolysis in a subject can provide a method of treating cancer. Inhibition of glycolysis can also be used in subjects to increase longevity (i.e., provide a prolongevity effect), including subjects that have not been diagnosed as having cancer. The inhibition of glycolysis can also be carried out to provide any of the other effects known to those skilled in the art, such as reducing insulin levels or stimulating autophagy.

Cancer Treatment Using Thiazolidinedione Derivatives

As noted herein, malignant cells exhibit significantly elevated glycolytic activity relative to normal cells, an effect referred to as the Warburg effect. Several mechanisms have been suggested to contribute to this effect, including mitochondrial defects, adaptation to the hypoxic environment in cancer tissues, oncogenic signals, and the abnormal expression of certain metabolic enzymes. Because the ability of cancer cells to use the mitochondrial respiratory machinery to generate ATP is reduced, cancer cells are forced to increase their glycolytic activity to maintain sufficient ATP generation for continued growth. This metabolic adaptation renders the cancer cells dependent on the glycolytic pathway and vulnerable to its inhibition. Furthermore, since this metabolic alternation is nearly ubiquitous in cancer cells, targeting the glycolytic pathway represents a useful method for treating a wide variety of different types of cancer. For further discussion of the use of glycolysis inhibition for anticancer treatment, see Pelicano et al., Oncogene, 25, p. 4633-4646 (2006).

When glycolysis is inhibited, the intact mitochondria in normal cells enable them to use alternative energy sources such as fatty acids and amino acids to produce metabolic intermediates which are channeled to the tricarboxylic acid cycle for ATP production through respiration. As a result, cells with normal mitochondria are less sensitive to agents that inhibit glycolysis, relative to cancer cells, providing therapeutic selectivity. Accordingly, the invention provides a method of treating cancer using thiazolidinedione derivatives as a result of their ability to selectively inhibit glycolysis in cancer cells.

The invention provides a method of treating cancer in a subject in need thereof. The method involves administering to the subject a therapeutically effective amount of a compound according to Formula I:

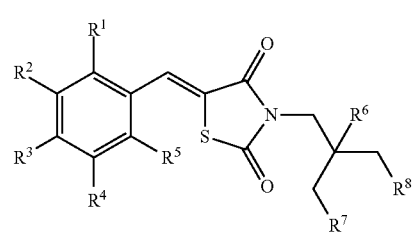

wherein $R^1$-$R^5$ are selected from the group consisting of hydrogen, $C_1$-$C_4$ alkyl, halogen, hydroxyl, nitro, amine, $C_1$-$C_4$ alkoxy, and trifluoromethyl; $R^6$ is selected from the group consisting of hydrogen, halogen, and $C_1$-$C_4$ alkyl; and $R^7$ and $R^8$ are $C_1$-$C_4$ alkyl, $C_1$-$C_4$ cycloalkyl or trifluoromethyl; and pharmaceutically acceptable salts thereof. In further embodiments, the compound is administered in a pharmaceutically acceptable carrier.

All of the compounds encompassed by formula I are considered to be described herein, and are suitable for use in the treatment of cancer. In some embodiments, the compounds of formula I are further defined such that $R^1$, $R^4$, and $R^5$ are hydrogen, which in other embodiments $R^7$ and $R^8$ are trifluoromethyl. In yet further embodiments, $R^2$ is trifluoromethyl and $R^3$ is hydroxyl.

In a preferred embodiment, compound 30, which is the structure shown below, is used for the treatment of cancer:

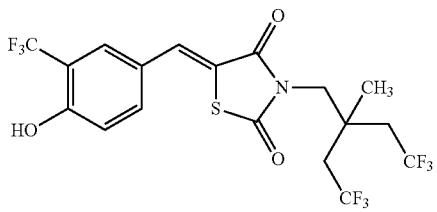 [SMILES: CC(CN1C(=O)S/C(=C\c2ccc(O)c(C(F)(F)F)c2)C1=O)(CC(F)(F)F)CC(F)(F)F]

A subject, as defined herein, is an animal, preferably a mammal such as a domesticated farm animal (e.g., cow, horse, pig) or a pet (e.g., dog, cat). More preferably, the subject is a human. The subject may also be a subject in need of cancer treatment. A subject in need of cancer treatment can be a subject who has been diagnosed as having a disorder characterized by unwanted, rapid cell proliferation. Such disorders include, but are not limited to cancers and precancerous conditions.

Thiazolidinedione derivatives can be used to both treat and prevent cancer. As used herein, the term "prevention" includes either preventing the onset of a clinically evident unwanted cell proliferation altogether or preventing the onset of a preclinically evident stage of unwanted rapid cell proliferation in individuals at risk. Also intended to be encompassed by this definition is the prevention of metastasis of malignant cells or to arrest or reverse the progression of malignant cells. This includes prophylactic treatment of those at risk of developing precancers and cancers.

Cancer cells contain genetic damage that has resulted in the relatively unrestrained growth of the cells. The genetic damage present in a cancer cell is maintained as a heritable trait in subsequent generations of the cancer cell line. The cancer treated by the method of the invention may be any of the forms of cancer known to those skilled in the art or described herein. Cancer that manifests as both solid tumors and cancer that instead forms non-solid tumors as typically seen in leukemia can be treated. Based on the prevalence of an increase in aerobic glycolysis in all types of cancer, the present invention provide methods for treating a subject that is afflicted with various different types of cancers, including carcinoma, sarcoma, and lymphoma. Examples of types of cancer that can be treated using the compounds of the invention include ovary, colon, lung, breast, thyroid, and prostate cancer, while additional embodiments are directed to only prostate cancer, breast cancer, and pancreatic cancer.

In some embodiments, the method is used to treat glucose receptor overexpressing cancers. Glucose receptor overexpressing cancers are cancers that are dependent on the presence of additional glucose receptors on the cancer cells to maintain the ability of the cells to proliferate. A wide variety of glucose transporter receptors are known to be involved in mediating glucose transport. Joost, H. G.; Thorens, B., Mol Membr Biol, 18, 247-56 (2001). In addition, a variety of different glucose transporters have been shown to be overexpressed in cancer cells. For example, GLUT1 overexpression has been shown to occur in ovary (Cantuaria et al., Cancer, 92, 1144-50 (2001)), colon (Haber et al., Cancer, 83, 34-40 (1998)), lung (Younes et al., Cancer, 80, 1046-51 (1997)), breast (Younes et al., Anticancer Res, 15, 2895-8 (1995)), thyroid (Haber et al., Thyroid, 7, 363-7 (1997)), and prostate (Stewart et al., Oncol Rep, 20, 1561-7 (2008)) cancers.

The effectiveness of cancer treatment may be measured by evaluating a reduction in tumor load or decrease in tumor growth in a subject in response to the administration of the thiazolidinedione derivative. The reduction in tumor load may be represent a direct decrease in mass, or it may be measured in terms of tumor growth delay, which is calculated by subtracting the average time for control tumors to grow over to a certain volume from the time required for treated tumors to grow to the same volume.

The compounds of the present invention may be administered alone or in conjunction with other antineoplastic agents or other growth inhibiting agents or other drugs or nutrients, as in an adjunct therapy. The phrase "adjunct therapy" or "combination therapy" in defining use of a compound described herein and one or more other pharmaceutical agents, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent.

For the purposes of combination therapy, there are large numbers of antineoplastic agents available in commercial use, in clinical evaluation and in pre-clinical development, which could be selected for treatment of cancers or other disorders characterized by rapid proliferation of cells by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplastic agents, such as metallomatrix proteases inhibitors (MMP), such as MMP-13 inhibitors, or $\alpha^v\beta_3$ inhibitors may be used. Suitable agents which may be used in combination therapy will be recognized by those of skill in the art. Similarly, when combination with radiotherapy is desired, radioprotective agents known to those of skill in the art may also be used. Treatment using compounds of the present invention can also be combined with treatments such as hormonal therapy, proton therapy, cryosurgery, and high intensity focused ultrasound (HIFU), depending on the clinical scenario and desired outcome.

Candidate agents may be tested in animal models. Typically, the animal model is one for the study of cancer. The study of various cancers in animal models (for instance, mice) is a commonly accepted practice for the study of human cancers. For instance, the nude mouse model, where human tumor cells are injected into the animal, is commonly accepted as a general model useful for the study of a wide variety of cancers (see, for instance, Polin et al., Investig. New Drugs, 15:99-108 (1997)). Results are typically compared between control animals treated with candidate agents and the control littermates that did not receive treatment. Transgenic animal models are also available and are commonly accepted as models for human disease (see, for instance, Greenberg et al., Proc. Natl. Acad. Sci. USA, 92:3439-3443 (1995)). Candidate agents can be used in these animal models to determine if a candidate agent decreases one or more of the symptoms associated with the cancer, including, for instance, cancer metastasis, cancer cell motility, cancer cell invasiveness, or combinations thereof.

Administration and Formulation of Thiazolidinedione Derivatives

The present invention provides a method for administering one or more thiazolidinedione derivatives in a pharmaceutical composition. Examples of pharmaceutical compositions include those for oral, intravenous, intramuscular, subcutaneous, or intraperitoneal administration, or any other route known to those skilled in the art, and generally involves providing the thiazolidinedione derivative formulated together with a pharmaceutically acceptable carrier.

When preparing the compounds described herein for oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitoneal administration, the compound may be combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

Formulations suitable for parenteral administration conveniently comprise a sterile aqueous preparation of the active compound which is preferably made isotonic. Preparations for injections may also be formulated by suspending or emulsifying the compounds in non-aqueous solvent, such as vegetable oil, synthetic aliphatic acid glycerides, esters of higher aliphatic acids or propylene glycol.

The dosage form and amount can be readily established by reference to known treatment or prophylactic regiments. The amount of therapeutically active compound that is administered and the dosage regimen for treating a disease condition with the compounds and/or compositions of this invention depends on a variety of factors, including the age, weight, sex, and medical condition of the subject, the severity of the disease, the route and frequency of administration, and the particular compound employed, the location of the unwanted proliferating cells, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administered may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight, may be appropriate. The daily dose can be administered in one to four doses per day.

For example, the maximum tolerated dose (MTD) for thiazolidinedione derivatives can be determined in tumor-free athymic nude mice. Agents are prepared as suspensions in sterile water containing 0.5% methylcellulose (w/v) and 0.1% Tween 80 (v/v) and administered to mice (7 animals/group) by oral gavage at doses of 0, 25, 50, 100 and 200 mg/kg once daily for 14 days. Body weights, measured twice weekly, and direct daily observations of general health and behavior will serve as primary indicators of drug tolerance. MTD is defined as the highest dose that causes no more than 10% weight loss over the 14-day treatment period.

The thiazolidinedione derivatives can also be provided as pharmaceutically acceptable salts. The phrase "pharmaceutically acceptable salts" connotes salts commonly used to form alkali metal salts and to form addition salts of free acids or free bases. The nature of the salt is not critical, provided that it is pharmaceutically acceptable. Suitable pharmaceutically acceptable acid addition salts of compounds of formula I may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, aralphatic, heterocyclic, carboxylic, and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, γ-hydroxybutyric, galactaric, and galacturonic acids. Suitable pharmaceutically acceptable base addition salts of the compounds described herein include metallic salts made from aluminum, calcium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used form base addition salts of the compounds described herein. All of these salts may be prepared by conventional means from the corresponding compounds described herein by reacting, for example, the appropriate acid or base with the compound.

Preparation of Thiazolidinedione Derivatives

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, Reagents for Organic Synthesis, v. 1-19, Wiley, New York, (1967-1999 ed.) and similar texts known to those skilled in the art. The preparation of various thiazolidinedione derivatives is described in earlier filed patent applications by the inventors. See U.S. Pat. No. 7,566,787 and U.S. Pat. No. 7,973,062, both by Chen et al., the disclosures of which are incorporated herein by reference in their entirety.

A variety of thiazolidinedione derivatives can also be prepared as shown in FIG. 1. Step (a) was carried out as follows. To a mixture of individual alcohols (1.1 eq.), thiazolidine-2,4-dione (1.0 eq.) and triphenyl phosphine (3.5 eq.) in dry THF, diisopropyl azo-dicarboxylate (DIPAD; 3.3 eq.) was added dropwise at 0° C. The reaction mixture was stirred at room temperature for 16 h, concentrated, dissolved in ethyl acetate, washed, in tandem, with water and brine, dried, and concentrated. The residue was purified by column chromatography (hexane-ethyl acetate) to afford various N-substituted thiazolidine-2,4-diones. For step (b), a mixture of individual di- and tri-substituted benzaldehydes (1.0 eq.), the corresponding N-substituted thiazolidine-2,4-dione (1.15 eq.), and a catalytic amount of piperidine in ethyl alcohol was reflux until the reaction completed, as monitored by TLC, and concentrated. The residue was purified by column chromatography (hexane-ethyl acetate) to afford compounds 5-30. The identity of each of the compounds was confirmed by NMR.

The present invention is illustrated by the following examples. It is to be understood that the particular examples, materials, amounts, and procedures are to be interpreted broadly in accordance with the scope and spirit of the invention as set forth herein.

EXAMPLES

Example 1

Identification of Glucose Uptake Inhibitors

Earlier studies by the inventors demonstrated that the suppressive effect of compound 4 on AR expression was associated with its ability to mimic glucose starvation through the inhibition of glucose uptake to increase the expression level of the E3 ligase β-transducin repeat-containing protein (β-TrCP). Wei et al., J Biol Chem, 285, 9780-91 (2010). This upregulation facilitated the proteasomal degradation of the transcription factor Sp1, leading to the transcriptional repression of AR. Thus, compound 4 was used as a starting point to generate potent glucose uptake inhibitors.

Figure 2:
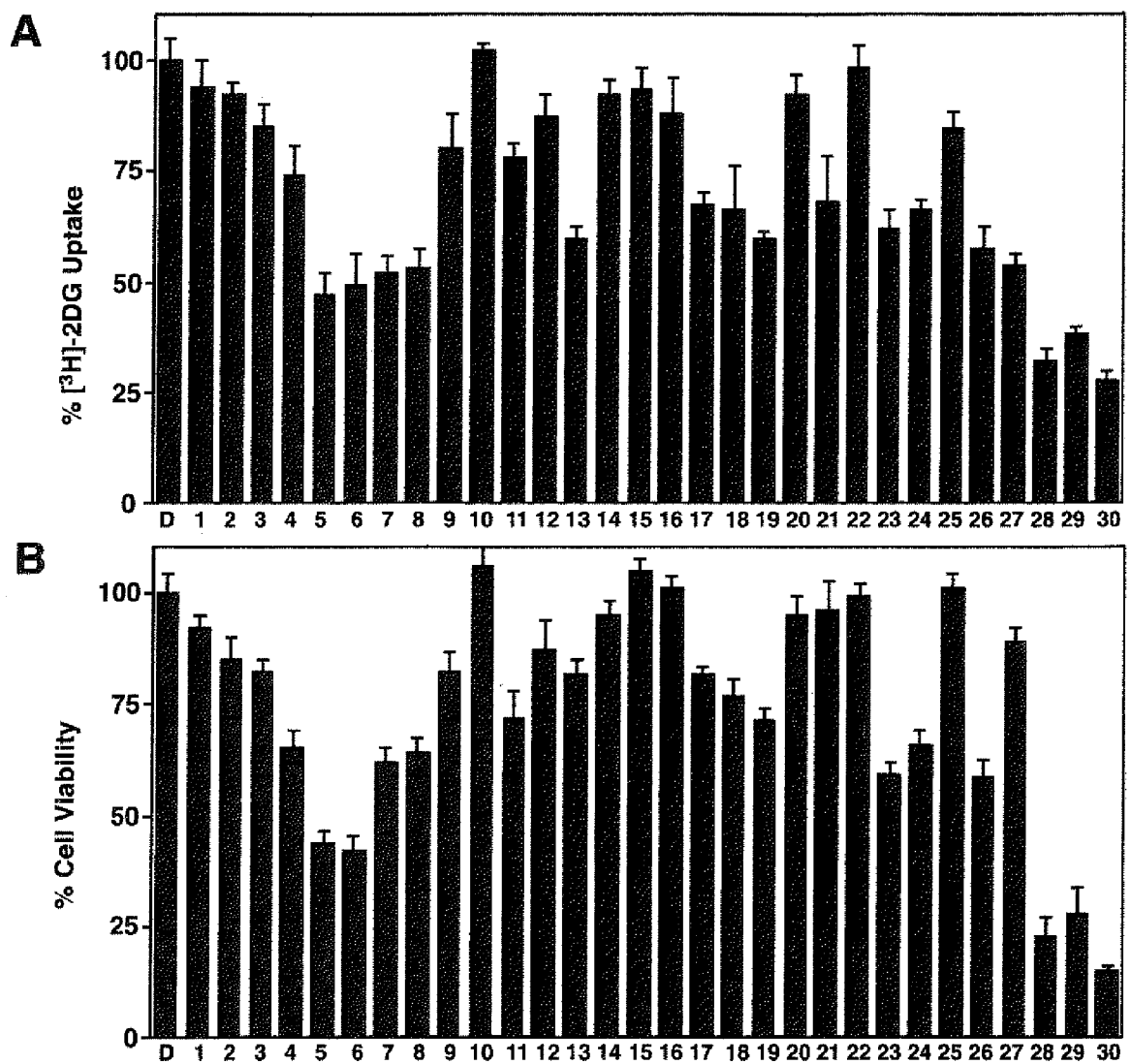
FIG. 2. (A) Inhibitory effects of compounds 1-30, each at 5 µM, on the uptake of [$^3$H]2-DG into LNCaP cells in Krebs-Ringer phosphate buffer at 37° C. after 30 min of drug treatment. Column, mean; bars, SD (N=3). (B) The corresponding effects on the viability of LNCaP cells by MTT assays in 10% FBS-containing RPMI 1640 medium after 72 h of drug treatment. Column, mean; bars, SD (N=6).

On the structural modification of compound 4, it was hypothesized that there exists interplay between the polar substituents on the phenyl ring and the terminal hydrophobic moiety in regulating its glucose uptake inhibitory activity. Accordingly, the methylcyclohexyl moiety of compound 4 was replaced by a series of hydrophobic moieties with varying degrees of bulkiness, generating compounds 5-9, among which compound 5 exhibited the most potent suppressive effect on the uptake of [$^3$H]2-deoxyglucose (2-DG) into LNCaP cells (FIG. 2A).

Compound 5 was subjected to further modifications via three different strategies: i) replacement of the electronegative —CF$_3$ function with various substituents (compounds 11-14) or rearrangement of the di-substituents on the phenyl ring (compounds 15 and 16), ii) substitution at the 5-position with various functional groups (compounds 17-22) or rearrangement of the tri-substituents on the phenyl ring (compounds 23-27), iii) replacement of the terminal —CH$_3$ functions of the hydrophobic side arm with —CF$_3$ to enhance electronegativity (compound 28) in conjunction with substitution of the tertiary proton with a F atom or —CH$_3$ group (compounds 29 and 30, respectively). General procedures for the synthesis of these compounds are depicted in FIG. 1B.

Results

Screening of the focused compound library to identify lead glucose uptake inhibitors. The aforementioned derivatives (5-30) along with the parent compounds (1-4), each at 5 μM, were assessed for their abilities to block the uptake of [$^3$H]2-DG into LNCaP cells after 30 min of exposure, which revealed a subtle structure-activity correlation (FIG. 2A).

The role of the hydrophobic side chain in regulating the glucose uptake-inhibitory potency was manifested by the differential activities among compounds 4-9, which showed an inverse correlation with the bulkiness of the hydrophobic moiety. Especially, the large discrepancy in the inhibitory potency between compounds 5-8 and 4/9 underscored the preferential recognition of ligands with smaller hydrophobic side chains by target proteins. Based on this consideration, compound 5 was selected as the lead agent for further modifications.

Evidence indicates that the ligand binding entailed hydrophilic interactions with the polar substituents on the terminal phenyl ring. For example, masking of the —OH substituent of the terminal phenyl ring of compound 5 with a methyl group (compound 10) abrogated the inhibitory activity. Moreover, the adjacent —CF$_3$ function could only be replaced with —NO$_2$ (13), but not —OH (11), —CH$_3$ (12), or —NH$_2$ (14), without compromising the drug activity, suggesting the involvement of electronegative function in protein-ligand interactions. This premise was also supported by lack of inhibitory activity in compounds 15 and 16, both of which lacked an electronegative substituent on the phenyl ring.

Introduction of an additional electron-withdrawing group, such as —F (17), —Br (18), or —NO$_2$ (21), or a —OH function (19) on the 5-position led to a modest decrease in the glucose uptake activity compared to the parent compound 5. However, substitution with —OCH$_3$ (20) or —NH$_2$ (22) resulted in a complete loss of activity. Compound 19's regioisomers, 23 and 24, showed similar potency as their parent molecule, indicating flexibility in ligand recognition. In line with the aforementioned premise, replacement of the —CF$_3$ of compound 23 with a —Br atom (25) substantially reduced the inhibitory activity, which, however, was contradicted by the similar potency between the pair of 24 to 26. This discrepancy suggested the role of the catechol moiety of 26 in interacting with target protein(s), which was corroborated by the ability of its regioisomer 27 to block glucose uptake with similar potency. These catechols, however, were not amenable to drug development due to intrinsic chemical/metabolic instability.

Considering the enhancing effect of the CF$_3$ moiety on the activity and metabolic stability of drug candidates in the course of lead optimization, 18-20 we replaced the two terminal methyl functions at the hydrophobic side chain of compound 5 with CF$_3$ groups with or without substitution at the tertiary carbon, leading to 28-30. All of these derivatives showed substantially improved potency relative to compound 5, in the relative order of 30>28>29. These compounds have the following nomenclature: Compound 28—5-(4-Hydroxy-3-trifluoromethyl-benzylidene)-3-[4,4,4-trifluoro-2-(2,2,2-trifluoro-ethyl)-butyl]-thiazolidine-2,4-dione; Compound 29—5-(4-Hydroxy-3-trifluoromethyl-benzylidene)-3-[2,4,4,4-tetrafluoro-2-(2,2,2-trifluoro-ethyl)-butyl]-thiazolidine-2,4-dione; and Compound 30—5-(4-Hydroxy-3-trifluoromethyl-benzylidene)-3-[4,4,4-trifluoro-2-methyl-2-(2,2,2-trifluoro-ethyl)-butyl]-thiazolidine-2,4-dione.

Additional candidate agents will be tested to evaluate the effect of thiazolidinedione derivatives in which the two terminal methyl functions of the hydrophobic side chain have been replaced with cycloalkyl groups. In some embodiments, the cycloalkyl groups are lower alkyl (i.e., $C_1$-$C_4$) cycloalkyl groups. In further embodiments, the cycloalkyl groups include one or more halogens. For example, the terminal methyl functions in some embodiments can be replaced with fluoro cyclopropyl groups. It is believed that thiazolidinedione derivatives bearing cycloalkyl groups, particularly those that are halogenated, will exhibit both high activity and bioavailability.

MTT assays indicate that the abilities of these thiazolidinedione derivatives to suppress the viability of LNCaP cell paralleled the respective activities in inhibiting glucose uptake (FIG. 2B), suggesting a potential causal relationship between these two cellular events.

Figure 3:
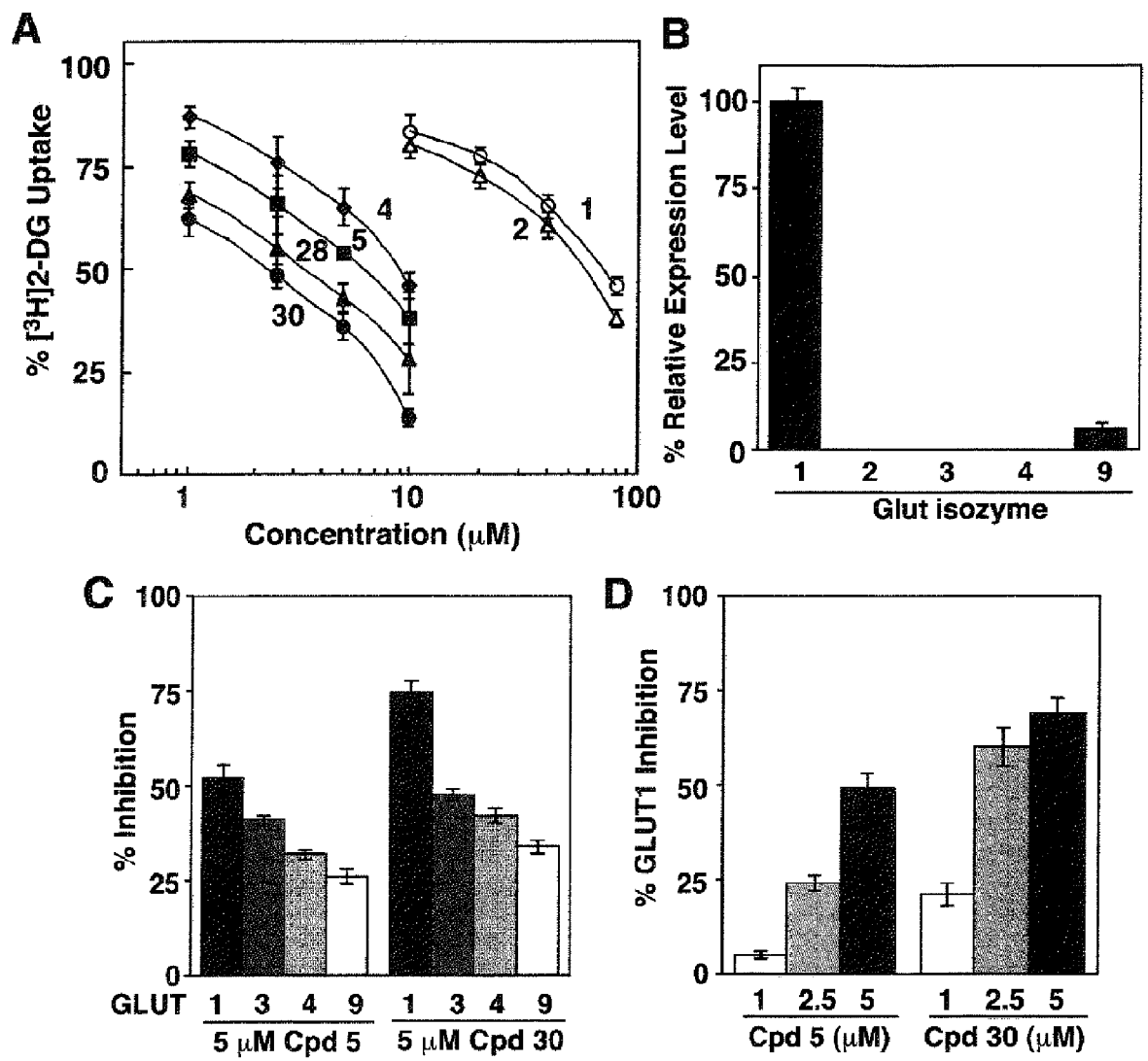
FIG. 3. (A) Dose-dependent inhibitory effects of compounds 1, 2, 4, 5, 28, and 30 on [$^3$H]2-DG into LNCaP cells in Krebs-Ringer phosphate buffer at 37° C. after 30 min of drug treatment. Column, mean; bars, SD (N=3). (B) qRT-PCR analysis of the differential expression of GLUT members 1-4 and 9 in LNCaP cells. Column, mean; bars, SD (N=3). (C) Suppressive effects of compounds 5 and 30, each at 5 µM, on [$^3$H]2-DG uptake into LNCaP cells overexpressing GLUT1, GLUT3, GLUT4, or GLUT9. The analysis was carried out in Krebs-Ringer phosphate buffer at 37° C. after 30 min of drug treatment. Column, mean; bars, SD (N=3). (D) Dose-dependent suppressive effects of compound 5 and 30 on [$^3$H]2-DG uptake into LNCaP cells overexpressing GLUT1. Column, mean; bars, SD (N=3).

Suppression of glucose uptake through the inhibition of glucose transporters. Dose response analysis confirmed the high potency of compound 30 in blocking [$^3$H]2-DG uptake into LNCaP cells with IC$_{50}$ of 2.5 μM, while the IC$_{50}$ values of other compounds examined were as follows: 28, 3.5 μM; 5, 6 μM; 4, 9 μM; 2, 52 μM; 1, 78 μM (FIG. 3A). Glucose transport across the cytoplasmic membrane is mediated by members of the facilitative glucose transporter/solute carrier (GLUT/SLC2A) family. Joost, H. G.; Thorens, B., Mol Membr Biol, 18, 247-56 (2001) To date, a total of 14 members have been identified, which are divided into three classes: class I, GLUTs1-4 and GLUT14; class II, GLUT5, GLUT7, GLUT9, and GLUT11; class III, GLUT6, GLUT8, GLUT10, GLUT12, and H$^+$-couple myo-inositol transporter.

As information regarding the expression pattern of individual GLUT members in LNCaP cells was lacking, quantitative real time polymerase chain reaction (qRT-PCR) was used to assess the mRNA levels of the hypoxia-responsive GLUT1 and GLUT3, and three other representative GLUT members, including the class I GLUT2 and GLUT4 and the class II GLUT9. Among these five members, LNCaP cells expressed GLUT1 and, to a much lesser extent, GLUT9, while the mRNA levels of GLUTs2-4 were negligible (FIG. 3B). To examine the isoform specificity of these inhibitors, LNCaP cells were ectopically transfected with plasmids encoding GLUT1, GLUT3, GLUT4, or GLUT9 vis-à-vis the pCMV control vector so that the increased glucose uptake in GLUT-transfected cells relative to pCMV control cells was indicative of the activity of the ectopically expressed GLUT protein. Among the four GLUT members examined, compounds 5 and 30, at 5 μM, displayed preferential inhibition of GLUT1 (53% and 73%, respectively), followed by GLUT3 (41% and 48%, respectively), GLUT4 (32% and 42%, respectively), and GLUT9 (26% and 34%, respectively) (FIG. 3C). The $IC_{50}$ values for compounds 5 and 30 in inhibiting GLUT1-mediated [$^3$H]2-DG uptake were 5 μM and 2 μM, respectively (FIG. 3D), similar to those determined in suppressing glucose uptake in LNCaP cells (FIG. 3A).

Figure 4:
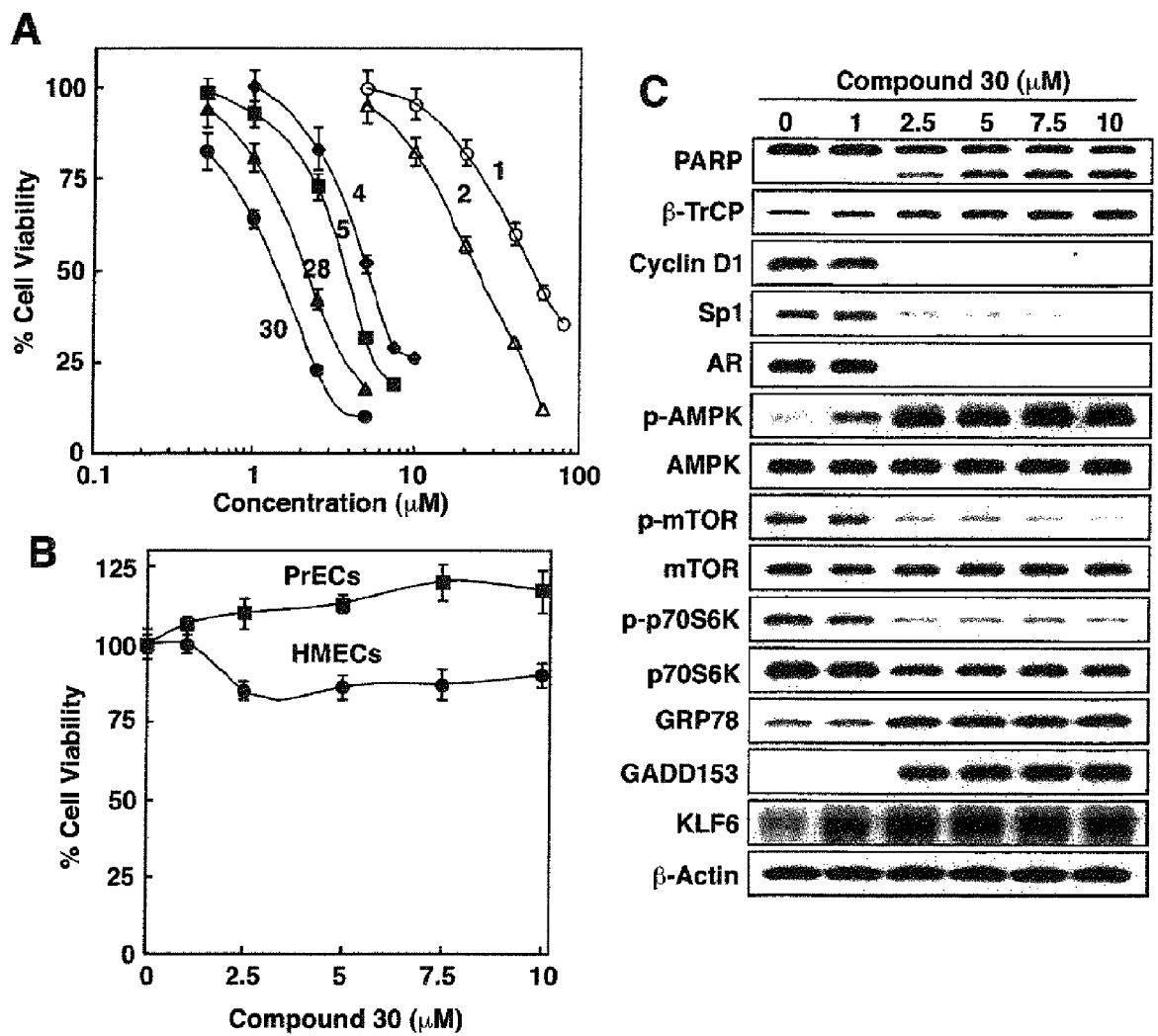
FIG. 4. (A) Dose-dependent suppressive effects of compounds 1, 2, 4, 5, 28, and 30 on the viability of LNCaP cells by MTT assays in 10% FBS-containing RPMI 1640 medium after 72 h of drug treatment. Column, mean; bars, SD (N=6). (B) Dose-dependent effect of compound 30 on the viability of normal prostate epithelial cells (PrECs) and human mammary epithelial cells (HMECs) after 72 h of treatment. Column, mean; bars, SD (N=6). (C) Western blot analysis of the dose-dependent effects of compound 30 on markers associated with apoptosis (PARP cleavage), β-TrCP-mediated protein degradation (β-TrCP, cyclin D1, Sp1, and AR), AMPK activation (p-AMPK, p-mTOR, and pp706SK), ER stress (GRP78 and GADD153), and epigenetic activation of KLF6.

The high antiproliferative potency of compound 30 is associated with its ability to elicit energy restriction-associated cellular responses. Examinations of the dose-dependent suppressive effects of compounds 28 and 30 versus compounds 1, 2, 4, and 5 on the viability of LNCaP cells revealed differential antiproliferative potencies that paralleled the respective inhibitory activities in glucose uptake (FIG. 4A). After 72 h of exposure in 10% fetal bovine serum (FBS)-containing medium, the $IC_{50}$ values for individual compounds were: 30, 1.5 μM; 28, 2.2 μM; 5, 4.2 μM; 4, 6 μM; 2, 28 μM; 1, 60 μM. It is noteworthy that despite the high potency of the optimal agent compound 30 in suppressing the viability of LNCaP cells, normal human prostate epithelial cells (PrECs) and human mammary epithelial cells (HMECs) were resistant to the cytotoxic effect of compound 30 even at 10 μM (FIG. 4B).

This drug-induced cell death was, at least in part, attributable to apoptosis, as evidenced by a dose-dependent increase in PARP cleavage in response to compound 30 (FIG. 4C). Equally important, compound 30 shared the reported activities of compound 4, 2-DG, and glucose starvation in eliciting energy restriction-associated cellular responses in LNCaP cells, including β-TrCP-facilitated protein degradation, adenosine monophosphate-activated protein kinase (AMPK), and endoplasmic reticulum (ER) stress. Chen et al., J Biol Chem, 286, 9968-76 (2011). Western blot analysis indicates that compound 30 dose dependently increased β-TrCP expression, leading to the downregulation of the expression of its substrates cyclin D1 and Sp1 as well as the Sp1 target AR (FIG. 4C). Furthermore, as AMPK negatively regulates the activation status of mammalian homologue of target of rapamycin (mTOR)-p70S6K signaling, the drug-facilitated increases in AMPK phosphorylation was accompanied by concomitant decreases in the levels of p-mTOR and p-p70S6K. Inoki et al., Cell 115, 577-90 (2003). Compound 30-induced ER stress was manifested by increased expression of the two ER stress markers: glucose-regulated protein (GRP)78 and growth arrest- and DNA damage-inducible gene (GADD)153. Moreover, reminiscent with the demonstrated effect of compound 4 on the epigenetic activation of KLF6, compound 30 increased the expression of this tumor suppressor protein in a dose-dependent manner.

Figure 5:
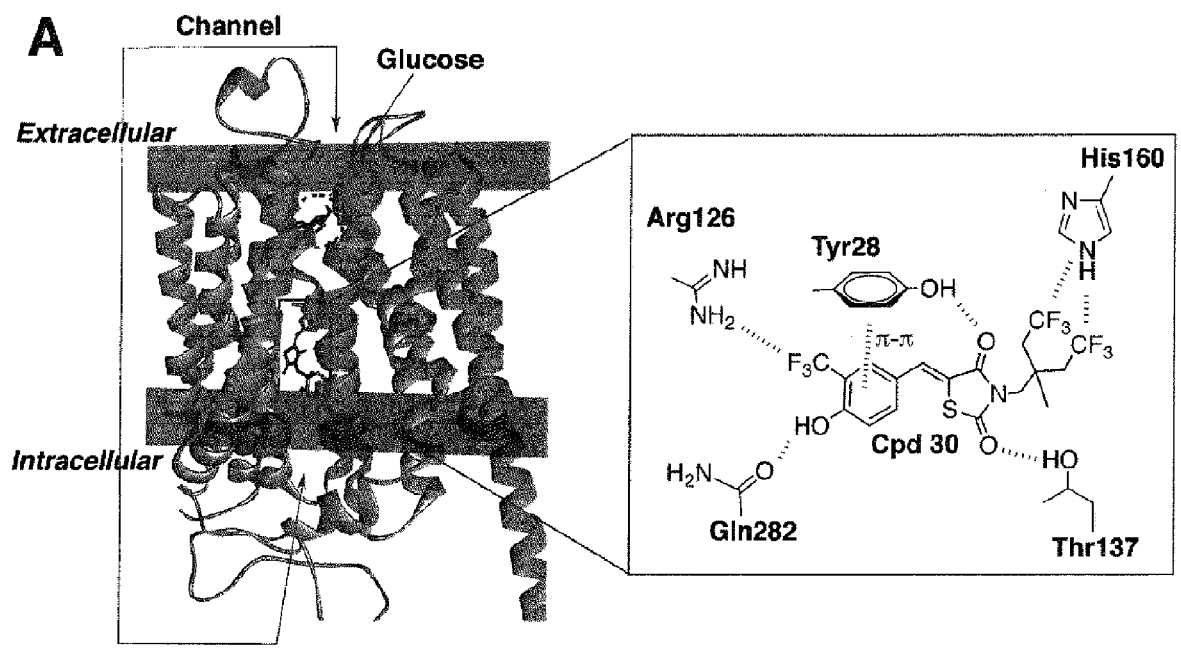
FIG. 5. (A) Left panel, provides a schematic representation of the predicted binding mode of compound 30 vis-à-vis that of glucose in the docking analysis of human GLUT1, showing that these two molecules bind to the transmembrane channel region at distinct sites. Right panel, Representation of the GLUT1 residues surrounding the docked compound 30, showing the potential electrostatic and π-π stacking interactions (dashed lines). (B) provides a representation of the GLUT1 residues surrounding the docked phenoxide species of compound 30, showing the potential electrostatic and π-π stacking interactions (dashed lines).
Figure 5:
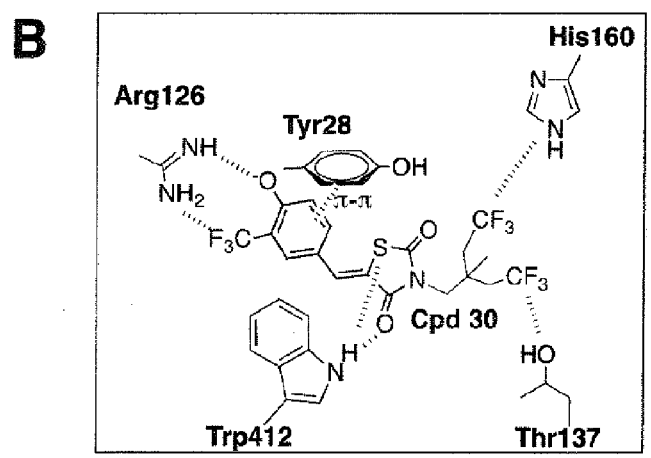

Modeling analysis of ligand binding. Modeling analysis was conducted to envisage the mode of ligand binding using the homology-modeled structure of the human GLUT1 [Protein Data Bank (PDB) code: 1SUK], which was developed using glycerol phosphate transporter as a template. Salas-Burgos, Biophys J, 87, 2990-9 (2004). Blind docking simulations revealed that compound 30 and glucose bound to distinct sites in the intermembrane channel of GLUT1 for glucose passage (FIG. 5A). While the glucose-recognition site was located near the channel opening, compound 30 bound to the central segment of the channel. Docking analysis indicates that compound 30 interacted with the putative binding site through electrostatic and π-π stacking interactions with Tyr28, Arg126, Thr137, His160, and Gln282 (FIG. 5B).

Discussion

In the course of malignant transformation, tumor cells gain growth advantage by increasing glucose consumption through aerobic glycolysis. Vander Heiden, Science, 324, 1029-1033 (2009). This reprogramming of energy metabolism is manifested by increased glucose uptake through the upregulation of glucose transporters, especially the hypoxia-responsive GLUT1. Macheda, et al., J Cell Physiol, 202, 654-62 (2005). From a clinical perspective, GLUT1 overexpression has been associated with poor prognosis of patients with various types of cancers, including those of ovary, colon, lung, breast, and thyroid, and with high Gleason grades in patients with prostate cancer.

Figure 6:
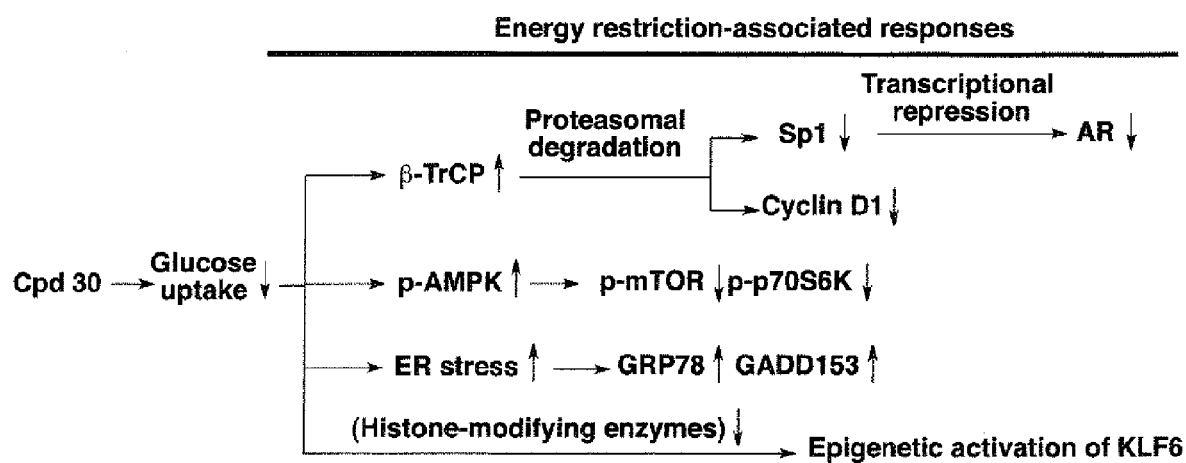
FIG. 6. Schematic diagram depicting the mode of action of compound 30 in eliciting energy restriction-associated cellular response FIG. 7. Effect of Compound 30 on the viability of human prostate cancer cell lines and nonmalignant prostate epithelial cells (PrEC). Cells were treated for 72 h with Compound 30 at the indicated concentrations in the presence of 10% FBS. Cell viabilities were determined by MTT assay. Points, mean (N=6); Bars, SD.

The use of thiazolidinediones as a scaffold to develop a novel class of glucose transporter inhibitors is described herein. The optimal agent compound 30 exhibited high potency in suppressing the [$^3$H]-2DG uptake and viability of LNCaP cells, with $IC_{50}$ values of 2.5 μM and 1.5 μM, respectively, which represents at a 40-fold improvement over that of compound 1. Equally important, compound 30 exhibited no appreciable cytotoxicity in PrECs and HMECs, indicating its discriminating effect between malignant and normal epithelial cells. Among the four GLUT members examined, compound 30 preferentially inhibited GLUT1-mediated [$^3$H]2-DG uptake with $IC_{50}$ of 2 μM versus that of ≥5 μM for GLUT3, GLUT4, and GLUT9. The effectiveness of compound 30 in GLUT1 inhibition underlies its high potency in triggering energy restriction-associated cellular responses in LNCaP cells, leading to changes in the functional status of an array of signaling proteins governing cell cycle progression and apoptosis (FIG. 6).

Docking modeling analysis suggests that the inhibitory effect of compound 30 on glucose entry was attributable to its ability to bind to the GLUT1 channel at a unique site distinct from that of glucose. This docking analysis provides a structural basis to account for the subtle structure-activity relationship among various derivatives of compound 5. For example, compounds 28-30 exhibited higher potencies than compound 5 in GLUT1 inhibition, in part, due to the additional electrostatic interactions between the two terminal —CF$_3$ functions with His160 and Thr137. Similarly, relative to compounds 28 and 29, the —CH$_3$ substituent on the tertiary carbon of compound 30 might have a steric effect on the configuration the two —CF$_3$ functions to allow closer interactions with His160 and Thr137 for tighter binding. Also noteworthy is the role of the —CF$_3$ function on the phenyl ring in mediating electrostatic interactions with Arg126, which might account for the loss of glucose uptake inhibitory activity when this electronegative moiety in compound 5 was replaced by —CH$_3$ (compound 12) or —NH$_2$ (compound 14).

Conclusion

The inventors have demonstrated that targeting aerobic glycolysis via the inhibition of glucose transporters represents a therapeutically relevant strategy for cancer treatment. In light of the high potency of compound 30 in suppressing glucose uptake, it serves as a useful agent to shed light onto the signaling pathways, at both cellular and epigenetic levels, by which caloric restriction induce cell death through apoptosis and autophagy in cancer cells.

Experimental Section

Unless otherwise indicated, all anhydrous solvents and chemical reagents were purchased at the highest grade available from Sigma-Aldrich (St. Louis, Mo.), and used without further purification. Flash column chromatography was performed with silica gel (230-400 mesh; Sorbent Technologies, Norcross, Ga.). Antibodies against various proteins were obtained from the following sources: Sp1, AR, Cyclin D1, phosphop70S6K (T389), p70S6K, GRP78, GADD153, KLF6 were from Santa Cruz (Santa Cruz, Calif.); β-TrCP was from Invitrogen; phospho-Thr-172-AMPK, AMPK, phospho-Ser-2448-mTOR, mTOR, PARP were from Cell Signaling Technology (Danvers, Mass.); β-actin was from MP Biomedicals (Irvine, Calif.). The general procedures for the synthesis of compounds 5-30 are depicted in FIG. 1B.

Cells and Cell Culture. LNCaP prostate cancer cells were obtained from the American Type Culture Collection (Manassas, Va.). Cells were maintained in 10% fetal bovine serum (FBS)-supplemented RPMI 1640 medium (Invitrogen, Carlsbad, Calif.). Normal human mammary epithelial cells (HMEC) and normal human prostate epithelial cells (PrEC) were obtained from Lonza (Walkersville, Md.) and were maintained in Mammary Epithelial Cell Growth Medium (MEGM) and Prostate Epithelial Cell Growth Medium (PrEGM) (Lonza, Walkersville, Md.), respectively.

Glucose Uptake Assay. LNCaP cells were seeded in six-well plates ($3\times10^5$ cells/well) for 24 h. Cells were washed twice with Krebs-Ringer phosphate buffer (126 mM NaCl, 2.5 mM KCl, 25 mM NaHCO$_3$, 1.2 mM NaH$_2$PO$_4$, 1.2 mM MgCl$_2$, 2.5 mM CaCl$_2$, pH 7.4) and were then treated with individual agents in Krebs-Ringer phosphate buffer. After 1.5 h, glucose uptake was initiated by adding 1 mL Krebs-Ringer buffer containing 1 mCi/mL [$^3$H]2-DG (PerkinElmer Life Science) and 100 mM non-radioactive 2-DG and was terminated by washing with cold PBS. The cells were lysed in 500 mL lysis buffer (10 mM Tris-HCl pH 8.0, 0.1% SDS) and aliquots were taken for measurement of radioactivity using a scintillation counter (Beckman LS6500).

Cell Viability Assay. Cell viability was determined using the 3-(4,5-dimethylthiazol-2-yl)-2,5-diphenyltetrazolium bromide (MTT) assay. Cancer cells were seeded at 5000 cells/well and normal cells were seeded at 8000 cells/well in 96-well plates and incubated in 10% FBS-supplemented medium for 24 h. Cells were then treated with individual agents for 72 h. Drug-containing medium was replaced with medium containing MTT (0.5 mg/mL), followed by incubation at 37° C. for 1 h. After removal of medium, the reduced MTT dye in each well was solubilized in 100 μL of DMSO and absorbance at 570 nm was measured.

Plasmid Construction, Transient Transfection and Immunoblotting. The full length GLUT1, GLUT4, and GLUT9 ORF cDNA clones were purchased from Addgene (Cambridge, Mass.) and GLUT3 ORF cDNA was purchased from Origene Technologies (Rockville, Md.). GLUT1, GLUT3, and GLUT9 were subcloned into the HindIII/SalI sites and GLUT4 was subcloned into the EcoRI/SalI sites of pEGFP-N2 expression vector (Clontech, Palo Alto, Calif.). Transfections were performed by electroporation using Nucleofector kit R of the Amaxa Nucleofector system (Lonza, Walkersville, Md.) according to the manufacturer's protocol. Immunoblotting was performed using cells lysates harvested with SDS lysis buffer (1% SDS, 50 mM Tris-HCl pH 8.0, 10 mM EDTA) containing 1× protease inhibitor cocktail (Sigma) and phosphatase inhibitor and were electrophoresed in 8~12% SDS polyacrylamide gels and then transferred onto nitrocellulose membranes. After blotting in 5% nonfat dry milk, the membranes were incubated with primary antibodies at 1:1,000 dilution in TBS-Tween 20 overnight at 4° C., and then secondary antibodies conjugated with horseradish peroxidase at 1:5,000 dilution in TBS-Tween 20 for 1 hour at room temperature. Protein bands were visualized on X-ray film using an enhanced chemiluminescence system.

Quantitative real-time polymerase chain reaction (PCR). Total RNA was isolated and reversed transcribed to cDNA using TRIzol reagent (Invitrogen) and the iScript cDNA Synthesis Kit (Bio-Rad Laboratories, Hercules, Calif.), respectively, according to the vendor's instructions. Real-time PCR was carried out in Bio-Rad CFX96 Real-Time PCR Detection System with iQ SYBR Green Supermix (Bio-Rad). Relative gene expression was normalized to 18s rRNA and calculated by using the published $2^{-\Delta\Delta Ct}$ method. Livak, K. J.; Schmittgen, T. D., Methods, 25, 402-8 (2001).

Molecular Docking Experiment. Docking was carried out using AutoDock 4.2. Molecular structure of compound 30 was prepared by the SYBYL 8.1 program (Tripos International, St. Louis, Mo., USA) using MMFF94 molecular mechanics force-field calculation. The coordinates for GLUT1 (PDB code 1SUK) were obtained by homology modeling based on glycerol phosphate transporter as a template. Salas-Burgos et al., Biophys J, 87, 2990-9 (2004). The initial blind docking using gird box of 100×100×126 points in three dimensions with a spacing of 0.6 Å centered on the whole GLUT1 indicated that the major interacting region was located in the channel. Accordingly, further docking simulations centering at channel using a gird box of 70×70×92 points in three dimensions with a spacing of 0.375 Å were applied to explore the binding behavior.

Example 2

Figure 7:
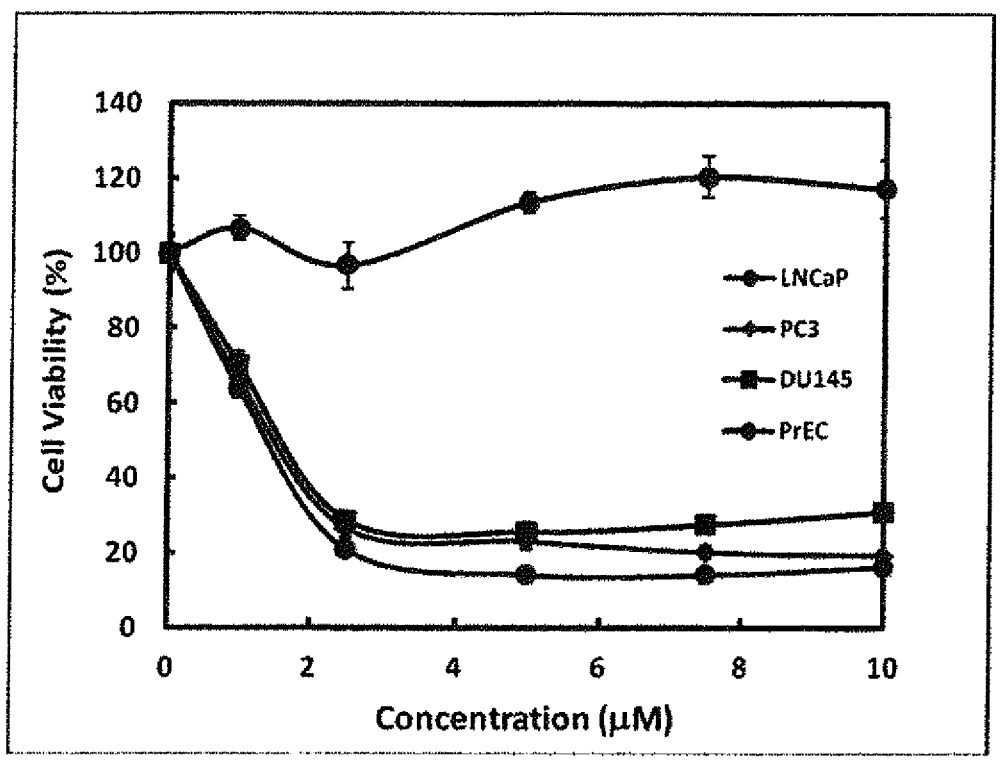

Antiproliferative Activity of Compound 30 in Human Prostate, Breast and Pancreatic Cancer Cell Lines Compound 30 was evaluated for antiproliferative activity in panels of different human cancer cells lines, including those of prostate, breast and pancreatic cancers. In all experiments, cells were treated with a range of concentrations of Compound 30 in the presence of 10% fetal bovine serum (FBS). Cell viability was then determined after 72 h of treatment using the 3-(4,5-dimethylthiazol-2-yl)-2,5-diphenyltetrazolium bromide (MTT) assay. As shown in FIG. 7, Compound 30 was equipotent in suppressing the viability of all three of the prostate cancer cells lines tested, which included the androgen-insensitive PC-3 and DU-145 cells, and the androgen-sensitive LNCaP cells, with IC$_{50}$ values of 1.5-1.7 μM. It is noteworthy that despite this high antiproliferative potency, normal human prostate epithelial cells (PrECs) were resistant to the cytotoxic effect of Compound 30 even at 10 μM.

Figure 8:
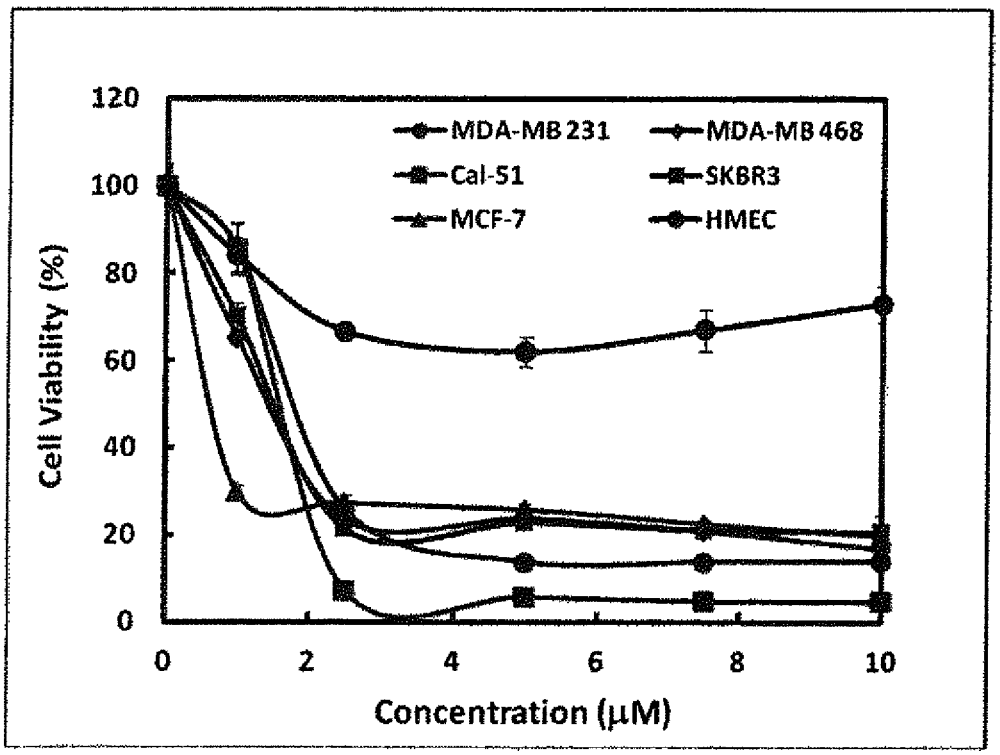
FIG. 8. Effect of Compound 30 on the viability of human breast cancer cell lines and nonmalignant mammary epithelial cells (HMEC). Cells were treated for 72 h with Compound 30 at the indicated concentrations in the presence of 10% FBS. Cell viabilities were determined by MTT assay. Points, mean (N=6); Bars, SD.

Among the five breast cancer cell lines tested, the estrogen receptor (ER)-positive MCF-7 cells were the most sensitive to the antiproliferative effects of Compound 30 with an IC$_{50}$ of about 0.7 μM (FIG. 8). Compound 30 also showed high activity against the other cell lines tested, including the HER2-overexpressing SKBR3 cells (IC$_{50}$, 1.6 μM) and those that represent the aggressive triple-negative subtype of breast cancer, MDAMB-468, Cal-51 and MDA-MB-231 cells ($IC_{50}$, 1.5, 1.7, and 1.9 µM, respectively). Importantly, like PrECs, nonmalignant human mammary epithelial cells (HMEC) were resistant to the effects of Compound 30 at concentrations up to 10 µM.

Figure 9:
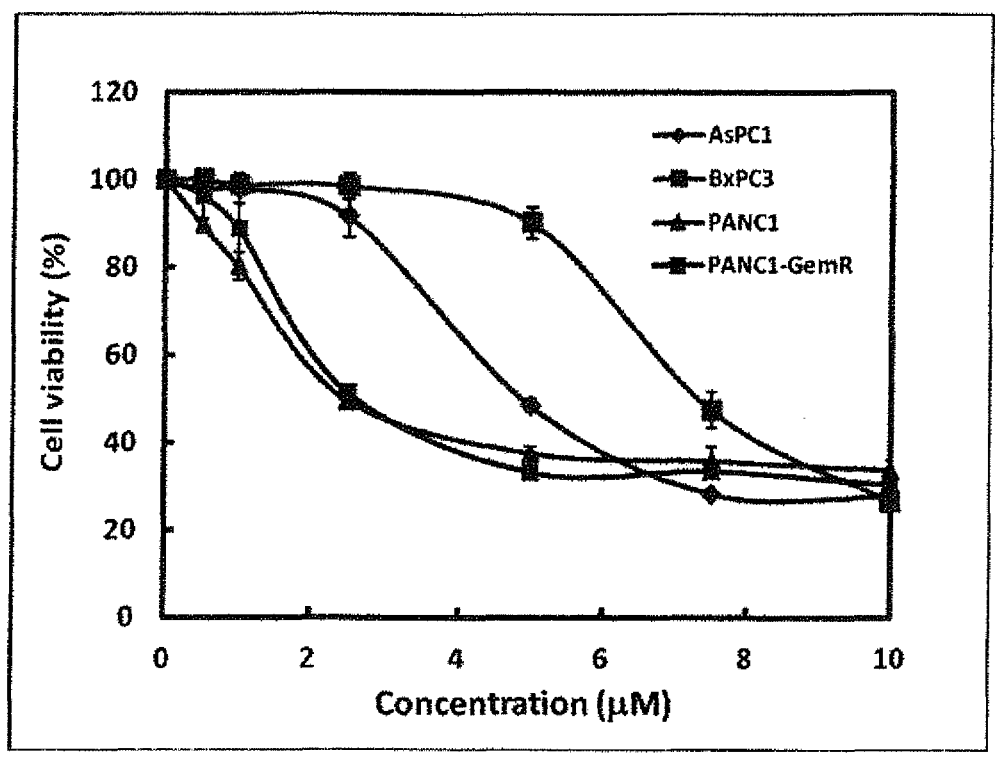
FIG. 9: Effect of Compound 30 on the viability of human pancreatic cancer cell lines. Cells were treated for 72 h with Compound 30 at the indicated concentrations in the presence of 10% FBS. Cell viabilities were determined by MTT assay. Points, mean (N=6); Bars, SD.

Relative to the prostate and breast cancer cell lines, the pancreatic cell lines evaluated showed greater variation in sensitivity to the antiproliferative effects of Compound 30. The AsPC1 and BxPC3 cells were the least sensitive of all of the cell lines tested, exhibiting $IC_{50}$ values of approximately 5 and 7.5 µM, respectively (FIG. 9). Of potential translational importance is that Compound 30 was equally potent against the PANC1 cell line and its gemcitabine-resistant subline PANC1-GemR with $IC_{50}$ values of approximately 2.5 µM for both lines.

The complete disclosure of all patents, patent applications, and publications, and electronically available materials cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A compound according to formula I:

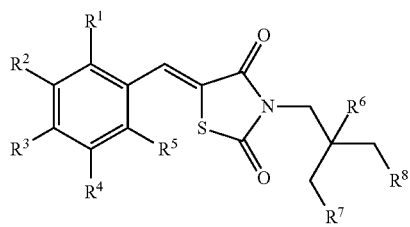

(I)

wherein $R^1$-$R^5$ are selected from the group consisting of hydrogen, $C_1$-$C_4$ alkyl, halogen, hydroxyl, nitro, amine, $C_1$-$C_4$ alkoxy, and trifluoromethyl;
$R^6$ is selected from the group consisting of hydrogen, halogen, and $C_1$-$C_4$ alkyl;
and $R^7$ and $R^8$ are trifluoromethyl;
and pharmaceutically acceptable salts thereof.

2. The compound according to claim 1, wherein $R^1$ and $R^5$ are hydrogen.

3. The compound according to claim 1, wherein $R^1$, $R^4$, and $R^5$ are hydrogen.

4. The compound according to claim 1, wherein $R^2$ is trifluoromethyl and $R^3$ is hydroxyl.

5. The compound according to claim 1, wherein the compound has the structure

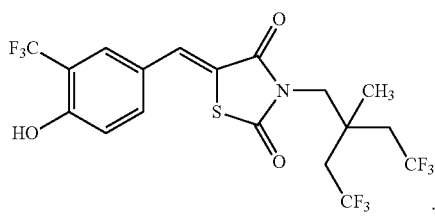

6. A method of treating cancer in a subject in need thereof, comprising administering to the subject a therapeutically effective amount of a compound according to Formula I:

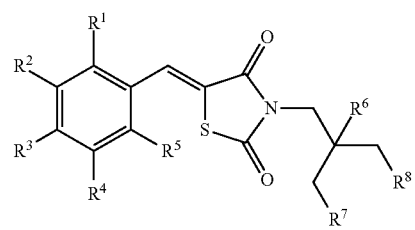

(I)

wherein $R^1$-$R^5$ are selected from the group consisting of hydrogen, $C_1$-$C_4$ alkyl, halogen, hydroxyl, nitro, amine, alkoxy, $C_1$-$C_4$ alkoxy, and trifluoromethyl;
$R^6$ is selected from the group consisting of hydrogen, halogen, and $C_1$-$C_4$ alkyl;
and $R^7$ and $R^8$ are trifluoromethyl;
and pharmaceutically acceptable salts thereof, wherein the cancer is selected from the group consisting of prostate cancer, breast cancer, and pancreatic cancer.

7. The method of claim 6, wherein $R^1$, $R^4$, $R^5$, and $R^6$ are hydrogen.

8. The method of claim 6, wherein $R^2$ is trifluoromethyl and $R^3$ is hydroxyl.

9. The method of claim 6, wherein the compound has the structure

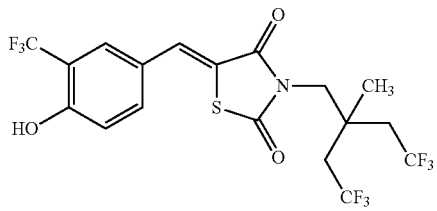 [SMILES: CC(CN1C(=O)S/C(=C\c2ccc(O)c(C(F)(F)F)c2)C1=O)(CC(F)(F)F)CC(F)(F)F]

10. The method of claim 6, wherein the subject is a human.

11. The method of claim 6, wherein the compound is administered in a pharmaceutically acceptable carrier.

12. A method of inhibiting glucose uptake in a cell by contacting the cell with a compound of formula I:

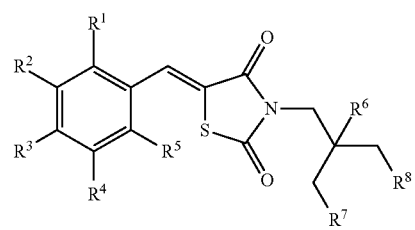

(I)

wherein $R^1$-$R^5$ are selected from the group consisting of hydrogen, $C_1$-$C_4$ alkyl, halogen, hydroxyl, nitro, amine, alkoxy, $C_1$-$C_4$ alkoxy, and trifluoromethyl;
$R^6$ is selected from the group consisting of hydrogen, halogen, and $C_1$-$C_4$ alkyl;
and $R^7$ and $R^8$ are trifluoromethyl;
and pharmaceutically acceptable salts thereof.

13. The method of claim 12, wherein the compound inhibits GLUT1-mediated glucose uptake.
14. The method of claim 12, wherein the cell is in vivo.
15. The method of claim 12, wherein the cell is in vitro.

* * * * *